US00PP24755P2

(12) United States Plant Patent
Irie

(10) Patent No.: US PP24,755 P2
(45) Date of Patent: Aug. 12, 2014

(54) *HYDRANGEA* PLANT NAMED 'YOUME H1917'

(50) Latin Name: *Hydrangea macrophylla*
Varietal Denomination: Youme H1917

(76) Inventor: Ryoji Irie, Kyoto (JP)

( * ) Notice: Subject to any disclaimer, the term of this patent is extended or adjusted under 35 U.S.C. 154(b) by 181 days.

(21) Appl. No.: 13/507,560

(22) Filed: Jul. 10, 2012

(51) Int. Cl.
*A01H 5/00* (2006.01)

(52) U.S. Cl.
USPC ..... Plt./250

(58) Field of Classification Search
CPC ..... A01H 5/02
USPC ..... Plt./250
See application file for complete search history.

(56) References Cited

PUBLICATIONS

Upov-Rom Pluto: Plant Variety Database 201305, retrieved on Feb. 25, 2014, retrieved from the Internet at <https://www3.wipo.int/pluto/user/en/index.jsp> for Hydrangea 'H19-17', 2 pp.*

* cited by examiner

*Primary Examiner* — June Hwu
(74) *Attorney, Agent, or Firm* — Penny J. Aguirre

(57) ABSTRACT

A new cultivar of *Hydrangea macrophylla* named 'Youme H1917' that is characterized by its free-flowering and re-blooming habit, and its large well-developed mop-head type inflorescences comprised of double sterile flowers with orbicular shaped sepals that are medium pink in color, and its fertile flowers that do not open.

2 Drawing Sheets

Genus/species: *Hydrangea macrophylla.*
Varietal denomination: 'Youme H1917'.

CROSS REFERENCE TO A RELATED APPLICATION

This application is co-pending with U.S. Plant Patent Applications filed for a plant derived from similar parentage in the Inventor's breeding program that are entitled *Hydrangea* Plant Named 'PERFECTION' (U.S. Plant Pat. No. 22,221), *Hydrangea* Plant Named 'FREEDOM' (U.S. Plant Pat. No. 22,210), and 'RIE 05' (U.S. Plant Pat. No. 18,508).

BACKGROUND OF THE INVENTION

The present invention relates to a new and distinct cultivar of *Hydrangea macrophylla* and will be referred to hereafter by its cultivar name, 'Youme H1917'. 'Youme H1917' represents a new bigleaf *hydrangea*, a perennial shrub grown for landscape use.

'Youme H1917' was derived from an ongoing controlled breeding program by the Inventor that focuses on developing new cultivars of bigleaf *hydrangeas* with unique flower colors and double flowers. 'Youme H1917' originated from a cross conducted in the Inventor's trial garden in June 1996 in Kyoto, Japan between an unnamed plant of *Hydrangea macrophylla* from the Inventor's breeding collection as the female parent and *Hydrangea macrophylla* 'Yamaajisai' (not patented) as the male parent. The new *Hydrangea* was selected as a unique single plant from the progeny of the cross in 2000.

Asexual reproduction of the new cultivar was first accomplished by softwood stem cuttings in Kyoto, Japan in 2000 by the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Youme H1917' as a unique cultivar of *Hydrangea macrophylla.*

1. 'Youme H1917' exhibits double sterile flowers that are medium pink in color with sepals that are orbicular in shape.
2. 'Youme H1917' exhibits a free flowering and repeating blooming habit; blooming from early May through early October in The Netherlands.
3. 'Youme H1917' exhibits large well-developed mop-head type inflorescences.
4. 'Youme H1917' is sterile; fertile flowers do not open.

'Youme H1917' can be compared to its male parent, 'Yamaajisai', which differs from 'Youme H1917' in having smaller flowers, in having a smaller flatter formed inflorescence, and in having weaker stems. 'Youme H1917' can be compared to its female parent, which differs from 'Youme H1917' in having fertile flowers that open and in having smaller inflorescences. 'Youme H1917' can be most closely compared to the cultivars 'FREEDOM', 'PERFECTION' and 'RIE 05. 'FREEDOM' differs from 'Youme H1917' in having whitish to light pink flowers. 'PERFECTION' differs from 'Youme H1917' in having inflorescences that are darker pink in color and in having sepals on the sterile flowers that are ovate in shape rather than orbicular. 'RIE 05' differs from 'Youme H1917' in having smaller flowers, smaller inflorescences, and flowers that are lighter pink in color.

BRIEF DESCRIPTION OF THE DRAWINGS

The photographs in the figures were taken of a two year-old plant of 'Youme H1917' as grown under greenhouse conditions with ambient light in a 5-liter container in De Kwakel, The Netherlands.

The photograph in FIG. 1 illustrates a side view of 'Youme H1917' in full bloom.

Figure 1:
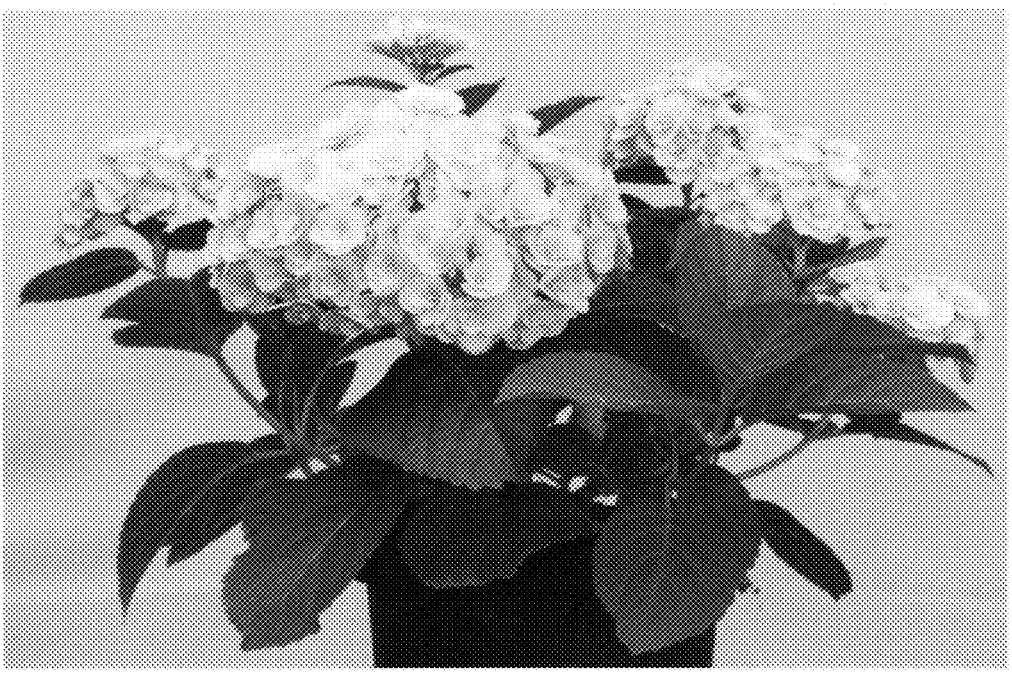
Figure 2:
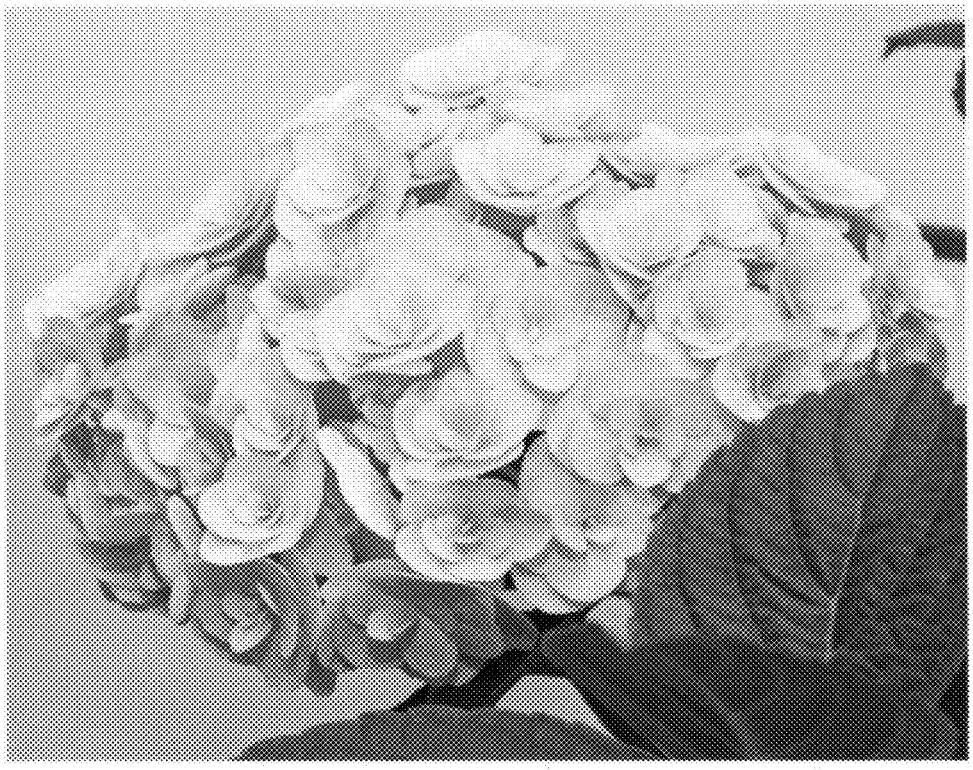

The photograph in FIG. 2 provides a close-up view of an inflorescence of 'Youme H1917'.

Figure 3:
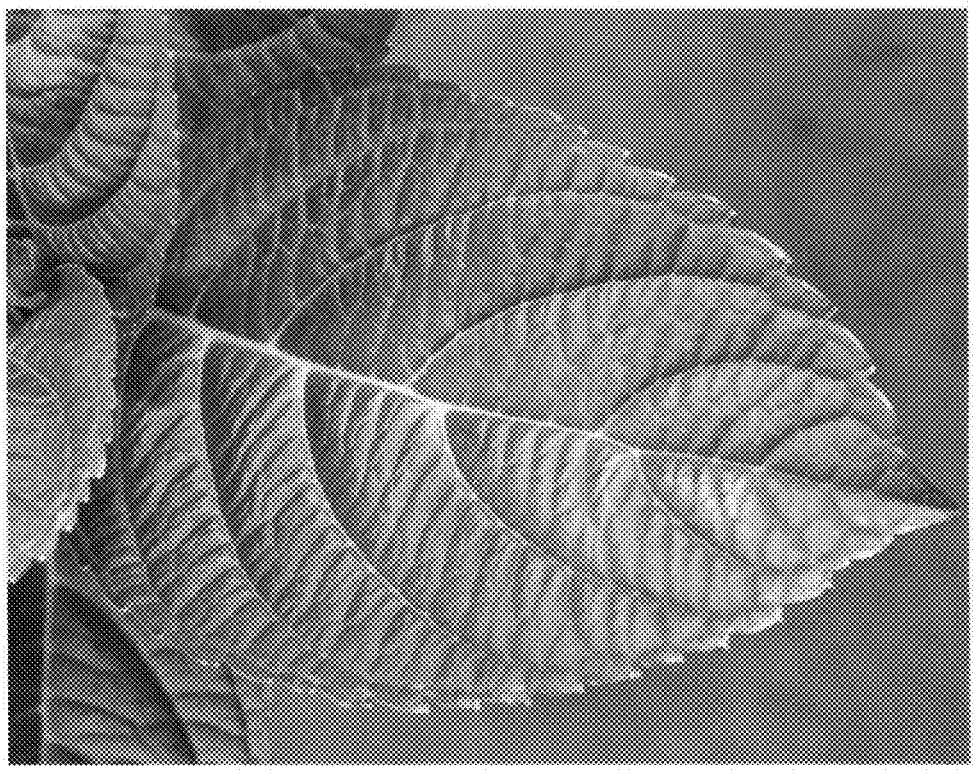

The photograph in FIG. 3 provides a close-up view of a leaf of 'Youme H1917'.

The colors in the photographs are as close as possible with the digital photography and printing techniques utilized and the color codes in the detailed botanical description more accurately describe the new *Hydrangea.*

BOTANICAL DESCRIPTION OF THE PLANT

The following is a detailed description of two year-old plants as grown under greenhouse conditions in five-liter containers in a greenhouse in De Kwakel, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Continuously from early May through October in The Netherlands.

*Plant habit.*—Broadly upright, deciduous shrub, sturdy, overall globular in shape.

*Height and spread.*—Average 30.4 cm in height and 61.7 cm in diameter.

*Hardiness.*—At least in U.S.D.A. Zones 4 to 9.

*Disease and pest resistance.*—Not more susceptible or resistant to pests and diseases than other *Hydrangea macrophylla* cultivars.

*Root description.*—Fibrous, dense.

Growth and propagation:

*Propagation.*—Softwood stem cuttings.

*Time required for root initiation.*—About 4 weeks during the summer and 5 weeks during the winter at an average temperature of 18° C. (night)/20° C. (day).

*Time required for root development.*—About 3 months to fully develop as a young plant when grown under greenhouse conditions at an average temperature of 18° C. (night)/20° C. (day) in summer or 8° C. (night)/12° C. (day) in winter.

*Time required to produce a salable crop.*—About 12 months from propagation to a flowering plant.

*Growth rate and vigor.*—Moderate, approximately 10 cm per month in spring.

Stem description:

*Stem shape.*—Round.

*Stem strength.*—Moderately strong.

*Stem aspect.*—Upright to an average angle of 45°.

*Stem color.*—Immature stem; 145A, mature stem; ranging between 199A to 199B and N199D.

*Stem size.*—Average of 18.6 cm in length and 6 mm in diameter.

*Stem surface.*—Smooth, moderately covered with narrow oblong lenticels, average of 1.5 mm in length and 0.5 mm in width, 183C to 183D in color.

*Branching.*—Moderately branching, with an average of 10 lateral branches.

*Internode length.*—Average of 5.5 cm.

Foliage description:

*Leaf shape.*—Ovate-eliptic.

*Leaf arrangement.*—Opposite.

*Leaf division.*—Simple.

*Leaf number.*—Average of 8 (4 pairs) per lateral branch.

*Leaf base.*—Obtuse to cordate.

*Leaf apex.*—Short apiculate.

*Leaf margins.*—Serrated.

*Leaf venation.*—Pinnate, upper surface; 144A, lower surface; 145B to 145C.

*Leaf size.*—Average of 13.7 cm in length and 9.8 cm in width.

*Leaf attachment.*—Petiolate.

*Leaf surface.*—Upper surface; slightly glossy and slightly rugose, lower surface dull.

*Leaf color.*—Immature upper surface; 143A, immature lower surface; 144A, mature upper surface; N137C, mature lower surface; 147B.

*Petioles.*—Average of 2.1 cm in length and 4 mm in width, upper surface; 145A to 145B in color, lower surface; 145A in color, both surfaces are smooth and slightly glossy.

Inflorescence description:

*Inflorescence type.*—Terminal globular, mophead, compound corymb of double rotate-shaped sterile flowers composed of an average of 15 sepals, fertile flowers form buds that do not open.

*Lastingness of inflorescence.*—Persistent with color lasting about 3 weeks.

*Inflorescence number.*—One per lateral or sublateral stem.

*Inflorescence size.*—Average of 9.5 cm in height and 16.9 cm in diameter (includes both the sterile flowers and fertile flower buds.

*Flower number.*—An average of 180 sterile flowers per inflorescence.

*Flower fragrance.*—None.

*Flower aspect.*—Upright and slightly outward.

*Flower size.*—Sterile flowers; rotate, average of 4 cm in diameter and 1.7 cm in depth, fertile flowers; do not open, remain as buds.

*Flower buds.*—Fertile flowers; an average of 3 mm in length and 2 mm in width, obovate in shape, 144C, top 144A in color, sterile flowers; an average of 9 mm in length and 6 mm in diameter, obovate in shape and 145C to 145D in color.

*Peduncles.*—Average of 5 cm in length and 15 mm in width, ranging from upright to a 40° angle to vertical, strong, 144A to 144B in color, glabrous surface.

*Pedicels.*—Fertile flowers; An average of 1 mm in length and 0.5 mm, held at an average angle of 15° to vertical, 144A to 144B in color, moderate strength, sparsely covered with very short hairs average length of 0.3 mm and NN155D in color, sterile flowers; an average of 3 cm in length and 2 mm in diameter, held at an average angle of 40° to vertical, 75B to 75C in color, moderate strength, sparsely covered with very short hairs average length of 0.3 mm and NN155D in color.

*Petals.*—Sterile flowers; 2 mm in diameter, color 68B on opening flowers, 75B on fully open flowers, and 69B on fading flowers, fertile flowers; remain closed in bud; 4, 3 mm in length and 0.5 mm in width, glabrous surface.

*Sepals.*—Sterile flowers; Average of 15, rotate in arrangement, both surfaces smooth and dull, obicular in shape, margin is entire, tip obtuse, base attenuate, an average of 1.7 cm in length and 1.7 cm in width, upper surface color when opening; 68B, lower surface color when opening; 73B to 73C, upper surface when fully open; 75B, lower surface when fully open; 75C, fading to upper side; 69B, fading to lower side; 69C to 69D, fertile flowers; 5, rotate in arrangement, ovate in shape, entire margin, acute apex, broad cuneate base, average of 2.5 mm in length and 0.15 mm in width, both surfaces are glabrous and dull, color of upper and lower surface when in bud 157C, dry and drop after bud is formed.

Reproductive organs:

*Androecium.*—Not developed, fertile flowers do not mature and drop once the buds are formed.

*Gynoecium.*—Not developed, fertile flowers do not mature and drop once the buds are formed.

*Fruit and seed.*—No seeds or fruit observed to date.

It is claimed:

1. A new and distinct cultivar of *Hydrangea* plant named 'Youme H1917' substantially as herein illustrated and described.

* * * * *